United States Patent [19]

Bhatnagar et al.

[11] Patent Number: 5,780,436
[45] Date of Patent: Jul. 14, 1998

[54] PEPTIDE COMPOSITIONS WITH GROWTH FACTOR-LIKE ACTIVITY

[75] Inventors: Rajendra S. Bhatnagar, Burlingame; Jing Jing Qian, San Bruno, both of Calif.

[73] Assignee: The Regents of the University of California, Oakland, Calif.

[21] Appl. No.: 742,256

[22] Filed: Oct. 31, 1996

Related U.S. Application Data

[63] Continuation-in-part of Ser. No. 431,954, May 1, 1995, Pat. No. 5,661,127.
[51] Int. Cl.[6] .................... A61K 38/04; A61K 38/08; C07K 7/06; C07K 5/10
[52] U.S. Cl. .................... 514/18; 514/17; 530/330; 530/329
[58] Field of Search .................... 514/17, 18, 16; 530/330, 329

[56] References Cited

U.S. PATENT DOCUMENTS

| | | | |
|---|---|---|---|
| 5,002,583 | 3/1991 | Pitaru et al. | 623/66 |
| 5,055,447 | 10/1991 | Palladino et al. | 514/12 |
| 5,158,934 | 10/1992 | Ammann et al. | 514/12 |
| 5,171,574 | 12/1992 | Kuberasampath et al. | 424/423 |
| 5,178,845 | 1/1993 | Constantz et al. | 423/305 |
| 5,208,219 | 5/1993 | Ogawa et al. | 514/12 |
| 5,236,905 | 8/1993 | Brankovan et al. | 514/12 |
| 5,240,912 | 8/1993 | Todaro | 514/12 |
| 5,258,029 | 11/1993 | Chu et al. | 623/16 |
| 5,268,455 | 12/1993 | Cianciolo | 530/404 |
| 5,270,300 | 12/1993 | Hunziker | 514/12 |
| 5,284,763 | 2/1994 | Derynk et al. | 435/240.1 |
| 5,322,933 | 6/1994 | Davies et al. | 530/399 |
| 5,324,519 | 6/1994 | Dunn et al. | 424/426 |
| 5,354,736 | 10/1994 | Bhatnagar et al. | 514/14 |
| 5,364,839 | 11/1994 | Gerhart et al. | 514/12 |
| 5,368,858 | 11/1994 | Hunziker | 424/423 |

FOREIGN PATENT DOCUMENTS

| | | |
|---|---|---|
| 93/09228 | 5/1993 | WIPO. |
| 93/09229 | 5/1993 | WIPO. |

OTHER PUBLICATIONS

Creighton TE. (1983) Proteins: Structures and Molecualr Properties. W.H. Freeman, New York.

Archer et al., "Transforming Growth Factor β1: Secondary Structure as Determined by Heteronuclear Magnetic Resonance Spectroscopy," *Biochemistry*, 32, (1993), pp. 1164–1171.

Basler et al., "Control of Cell Pattern in the Neural Tube: Regulation of Cell Differentiation by dorsalin-1, a Novel TGFβ Family Member," *Cell*, 73, (May 21, 1993), pp. 687–702.

Berge et al., "Pharmaceutical Salts," *Journal of Pharmaceutical Sciences*, 66:1, (Jan. 1977), pp. 1–19.

Bone et al., "Definitions for Sepsis and Organ Failure and Guidelines for the Use of Innovative Therapies in Sepsis," *Chest*, 101:6 (Jun. 1992), pp. 1644–1655.

Daopin et al., "Crystal Structure of TGF-β2 Refined at 1.8 Å Resolution," *Proteins*, 17, (1993), pp. 176–192.

Hubbell and Langer, "Tissue Engineering," *Chemical and Engineering News*, (Mar. 13, 1995), pp. 42–54.

Massagué, "The Transforming Growth Factor-β Family," *Annu. Rev. Cell Biol.*, 6, (1990), pp. 597–641.

Termine and Posner, "Calcium Phosphate Formation in vitro: I. Factors Affecting Initial Phase Separation," *Archives of Biochemistry and Biophysics*, 140, (1970), pp. 307–317.

Termine et al., "Calcium Phosphate Formation in vitro: II. Effects of Environment on Amorphous–Crystalline Transformation," *Archives of Biochemistry and Biophysics*, 140, (1970), pp. 318–325.

Amatayakul–Chantler et al., "[Ser[77]] Transforming Growth Factor-β1," *Journal of Biological Chemistry*, 269:44, (1994), pp. 27687–27691.

Chang et al., "Cartilage–derived Morphogenetic Proteins," *Journal of Biological Chemistry*, 269:45, (1994), pp. 28227–28234.

Chopra et al., "Newly Synthesized Proteoglycans Secreted by Sequentially Derived Populations of Cells from New–Born Rat Calvaria," *Cell Differentiation and Development*, 32, (1990), pp. 47–59.

Colletta et al., "The Growth Inhibition of Human Breast Cancer Cells by a Novel Synthetic Progestin Involves the induction fo Transforming Growth Factor Beta," *J. Clin. Invest.*, 87, (1991), pp. 277–283.

Galéra et al., "Effect of Transforming Growth Factor-β-1 (TGF-β1) on Matrix Synthesis by Monolayer Cultures of Rabbit Articular Chondrocytes during . . . ." *Experimental Cell Research*, 200 (1992), pp. 379–392.

Grande et al., "Transforming Growth Factor-β1 Induces Collagen IV Gene Expression in NIH–3T3 Cells," *Laboratory Investigation*, 69:4, (1993), pp. 387–395.

Günther et al., "Transforming Growth Factor β1 Regulates Tissue Inhibitor of Metalloproteinases–1 Expression in Differentiated Human Articular Chondrocytes," *Arthritis & Rheumatism*, 37:3, (1994), pp. 395–405.

(List continued on next page.)

*Primary Examiner*—Elizabeth C. Kemmerer
*Assistant Examiner*—David S. Romeo
*Attorney, Agent, or Firm*—Majestic, Parsons, Siebert & Hsue

[57] ABSTRACT

Small peptide mimics of TGF-β, having the general sequence $AA_i$-$AA_{i+1}$-$AA_{i+2}$ followed by $AA_{i+n}$ shortly thereafter, have been prepared. In this sequence, $AA_i$ is alanine, asparagine, or leucine, $AA_{i+1}$ is valine or isoleucine, $AA_{i+2}$ is alanine, n is 3, 4, or 5 such that there are n–3 amino acid residues in between $AA_{i+2}$ and $AA_{i+n}$, and $AA_{i+n}$ is glutamic acid, aspartic acid, glutamine or asparagine. Because the essential requirement for TGF-β activity is the peptide's ability to form a stable β-bend structure under physiologic conditions, the inventive peptides are collectively referred to as β-bend peptides. Compositions for applications such as tissue repair are also provided that comprise a biocompatible matrix having cytomodulin or a cytomodulin analog admixed with or carried by the matrix.

25 Claims, 9 Drawing Sheets

OTHER PUBLICATIONS

Hamilton and Millis, "Developmental Roles for Growth Factor-Regulated Secreted Proteins," *Current Topics in Developmental Biology*, 24, (1990), pp. 193–218.

Li and Drucker, "Growth Facator-like Properties of Parathyroid Hormone-related Peptide in Transfected Rodent Cell Lines," *Cancer Research*, 53, (1993), pp. 2980–2986.

Lynch and Giannobile, "Polypeptide Growth Factors: Molecular Mediator of Tissue Repair," Chapter 33 in *Molecular Pathogenesis of Periodontal Disease*, (1994), pp. 415–425.

Massagué et al., "Multiple Type-$\beta$ Transforming Growth Factors and Their Receptors," *Journal of Cellular Physiology Supplement*, 5, (1987), pp. 43–47.

Matrisian and Hogan, "Growth Factor-Regulated Proteases and Extracellular Matrix Remodeling during Mammalian Development," *Current Topics in Developmental Biology*, 24, (1990), pp. 219–259.

Nakanishi et al., "Expression of Nerve Growth Factor Family Neurotrophins in a Mouse Osteoblastic Cell Line," *Biochemical and Biophysical Research Communications*, 198:3, (1994), pp. 891–897.

Nogami et al., "Bioassay of Chondrocyte Differentiation by Bone Morphogenetic Protein," *Clinical Orthopaedics and Related Research*, 258, (1990), pp. 295–299.

O'Reilly et al., "Regulation of Expression of Transforming Growth Factor-$\beta$2 by Transforming Growth Factor-$\beta$ Isoforms is Dependent upon Cell Type," *Growth Factors*, 6, (1992), pp. 193–201.

Rosen et al., "Bone Induction and Transforming Growth Factor-$\beta$," *Annals New York Academy of Sciences*.

Rutherford et al., "Induction of Reparative Dentine Formation in Monkeys by Recombinant Human Osteogenic Protein–1," *Archs oral Biol.*, 38:7, (1993), pp. 571–576.

Sampath et al., "Recombinant Human Osteogenic Protein–1 (hOP–1) Induces New Bone Formation in Vivo with a Specific Activity Comparable with . . . " *Journal of Biological Chemistry*, 267:28, (1992), pp. 20352–20362.

Saunders and D'Amore, "FGF and TFG-$\beta$: Actions and Interactions in Biolgoical Systems," *Critical Reviews in Eukaryotic Gene Expression*, 1:3, (1991), pp. 157–172.

Schwarz et al., "Aberrant TGF-$\beta$ Production and Regulation in Metastatic Malignancy," *Growth Factors*, 3, (1990), pp. 115–127.

Segarini, Patricia R., "Cell Type Specificity of TGF-$\beta$ Binding," *Annals New York Academy of Sciences*.

Sporn et al., "Some Recent Advances in the Chemistry and Biology of Transforming Growth Factor–Beta," *Journal of Cell Biology*, 105, (1987), pp. 1039–1045.

Taketazu et al., "Enhanced Expression of Transforming Growth Factor-$\beta$s and Transforming Growth Factor-$\beta$ Type II Receptors . . . ," *Laboratory Investigation*, 70:5, (1994), pp. 620–630.

van Beuningen et al., "Transforming Growth Facator-$\beta$1 Stimulates Articular Chondrocyte Proteoglycan Synthesis and Induces Osteophyte Formation . . . ," *Laboratory Investigation*, 71:2, (1994), pp. 279–290.

Wozney et al., "Novel Regulators of Bone Formation: Molecular Clones and Activities," *Science*, 242, (1988), pp. 1528–1534.

Joyce et al., "Role of Transforming Growth Factor-$\beta$ in Fracture Repair," *Annals New York Academy of Sciences*.

CONTROL

FIG. 5-1

| | | | | | | |
|---|---|---|---|---|---|---|
| 1 | H1 | ACE | 1 | 1.952 | 1.249 | .316 |
| 2 | CH3 | ACE | 1 | 1.927 | 2.333 | .203 |
| 3 | H2 | ACE | 1 | 1.576 | 2.782 | 1.133 |
| 4 | H3 | ACE | 1 | 1.243 | 2.593 | -.605 |
| 5 | C | ACE | 1 | 3.323 | 2.853 | -.119 |
| 6 | O | ACE | 1 | 4.272 | 2.077 | -.210 |
| 7 | N | ALA | 2 | 3.439 | 4.166 | -.310 |
| 8 | HN | ALA | 2 | 2.632 | 4.767 | -.211 |
| 9 | CA | ALA | 2 | 4.695 | 4.857 | -.543 |
| 10 | HA | ALA | 2 | 5.425 | 4.521 | .195 |
| 11 | CB | ALA | 2 | 5.211 | 4.572 | -1.957 |
| 12 | HB1 | ALA | 2 | 4.475 | 4.894 | -2.694 |
| 13 | HB2 | ALA | 2 | 6.142 | 5.115 | -2.122 |
| 14 | HB3 | ALA | 2 | 5.399 | 3.506 | -2.083 |
| 15 | C | ALA | 2 | 4.443 | 6.350 | -.361 |
| 16 | O | ALA | 2 | 3.292 | 6.788 | -.383 |
| 17 | N | ASN | 3 | 5.504 | 7.130 | -.187 |
| 18 | HN | ASN | 3 | 6.426 | 6.699 | -.147 |
| 19 | CA | ASN | 3 | 5.484 | 8.570 | .015 |
| 20 | HA | ASN | 3 | 4.836 | 9.029 | -.733 |
| 21 | CB | ASN | 3 | 4.964 | 8.871 | 1.432 |
| 22 | HB2 | ASN | 3 | 5.670 | 8.464 | 2.158 |
| 23 | HB3 | ASN | 3 | 4.000 | 8.383 | 1.578 |
| 24 | CG | ASN | 3 | 4.760 | 10.357 | 1.704 |
| 25 | OD1 | ASN | 3 | 4.723 | 11.177 | .792 |
| 26 | ND2 | ASN | 3 | 4.654 | 10.739 | 2.969 |
| 27 | HND1 | ASN | 3 | 4.656 | 10.052 | 3.709 |
| 28 | HND2 | ASN | 3 | 4.487 | 11.714 | 3.168 |
| 29 | C | ASN | 3 | 6.925 | 9.054 | -.180 |
| 30 | O | ASN | 3 | 7.816 | 8.242 | -.407 |
| 31 | N | VAL | 4 | 7.196 | 10.354 | -.082 |
| 32 | HN | VAL | 4 | 6.433 | 11.007 | .038 |
| 33 | CA | VAL | 4 | 8.563 | 10.863 | -.110 |
| 34 | HA | VAL | 4 | 9.001 | 10.579 | -1.068 |
| 35 | CB | VAL | 4 | 8.546 | 12.404 | -.038 |
| 36 | HB | VAL | 4 | 7.922 | 12.763 | -.857 |
| 37 | CG1 | VAL | 4 | 7.958 | 12.951 | 1.272 |
| 38 | HG11 | VAL | 4 | 8.590 | 12.684 | 2.119 |
| 39 | HG12 | VAL | 4 | 7.900 | 14.038 | 1.213 |
| 40 | HG13 | VAL | 4 | 6.955 | 12.563 | 1.438 |
| 41 | CG2 | VAL | 4 | 9.949 | 12.988 | -.245 |
| 42 | HG21 | VAL | 4 | 10.376 | 12.608 | -1.174 |
| 43 | HG22 | VAL | 4 | 9.889 | 14.075 | -.306 |
| 44 | HG23 | VAL | 4 | 10.605 | 12.718 | .583 |

FIG. 5-2

| | | | | | | |
|---|---|---|---|---|---|---|
| 45 | C | VAL | 4 | 9.414 | 10.217 | .994 |
| 46 | O | VAL | 4 | 10.604 | 9.986 | .807 |
| 47 | N | ALA | 5 | 8.808 | 9.966 | 2.157 |
| 48 | HN | ALA | 5 | 7.829 | 10.176 | 2.244 |
| 49 | CA | ALA | 5 | 9.520 | 9.482 | 3.331 |
| 50 | HA | ALA | 5 | 10.411 | 10.096 | 3.479 |
| 51 | CB | ALA | 5 | 8.626 | 9.645 | 4.563 |
| 52 | HB1 | ALA | 5 | 7.723 | 9.042 | 4.457 |
| 53 | HB2 | ALA | 5 | 9.169 | 9.314 | 5.450 |
| 54 | HB3 | ALA | 5 | 8.350 | 10.693 | 4.688 |
| 55 | C | ALA | 5 | 9.968 | 8.025 | 3.185 |
| 56 | O | ALA | 5 | 11.076 | 7.684 | 3.587 |
| 57 | N | GLU | 6 | 9.079 | 7.168 | 2.682 |
| 58 | HN | GLU | 6 | 8.245 | 7.512 | 2.233 |
| 59 | CA | GLU | 6 | 9.204 | 5.720 | 2.725 |
| 60 | HA | GLU | 6 | 10.254 | 5.429 | 2.779 |
| 61 | CB | GLU | 6 | 8.456 | 5.210 | 3.964 |
| 62 | HB2 | GLU | 6 | 7.393 | 5.439 | 3.867 |
| 63 | HB3 | GLU | 6 | 8.837 | 5.712 | 4.854 |
| 64 | CG | GLU | 6 | 8.602 | 3.703 | 4.203 |
| 65 | HG2 | GLU | 6 | 9.655 | 3.443 | 4.313 |
| 66 | HG3 | GLU | 6 | 8.176 | 3.138 | 3.375 |
| 67 | CD | GLU | 6 | 7.861 | 3.290 | 5.467 |
| 68 | OE1 | GLU | 6 | 6.706 | 3.745 | 5.612 |
| 69 | OE2 | GLU | 6 | 8.468 | 2.548 | 6.266 |
| 70 | C | GLU | 6 | 8.583 | 5.188 | 1.438 |
| 71 | O | GLU | 6 | 7.633 | 5.781 | .930 |
| 72 | N | ASN | 7 | 9.123 | 4.107 | .882 |
| 73 | HN | ASN | 7 | 9.827 | 3.588 | 1.392 |
| 74 | CA | ASN | 7 | 8.673 | 3.542 | -.382 |
| 75 | HA | ASN | 7 | 7.595 | 3.676 | -.478 |
| 76 | CB | ASN | 7 | 9.390 | 4.236 | -1.545 |
| 77 | HB2 | ASN | 7 | 10.466 | 4.108 | -1.419 |
| 78 | HB3 | ASN | 7 | 9.155 | 5.301 | -1.530 |
| 79 | CG | ASN | 7 | 8.962 | 3.664 | -2.892 |
| 80 | OD1 | ASN | 7 | 7.842 | 3.197 | -3.055 |
| 81 | ND2 | ASN | 7 | 9.840 | 3.699 | -3.887 |
| 82 | HND1 | ASN | 7 | 10.757 | 4.091 | -3.746 |
| 83 | HND2 | ASN | 7 | 9.556 | 3.315 | -4.774 |
| 84 | C | ASN | 7 | 8.974 | 2.049 | -.371 |
| 85 | O | ASN | 7 | 9.950 | 1.634 | .253 |
| 86 | N | ALA | 8 | 8.148 | 1.245 | -1.035 |
| 87 | HN | ALA | 8 | 7.449 | 1.658 | -1.644 |

FIG. 5-3

| 88  | CA  | ALA | 8 | 8.215 | -.205  | -1.003 |
|-----|-----|-----|---|-------|--------|--------|
| 89  | HA  | ALA | 8 | 9.244 | -.529  | -.837  |
| 90  | CB  | ALA | 8 | 7.341 | -.717  | .150   |
| 91  | HB1 | ALA | 8 | 6.300 | -.440  | -.024  |
| 92  | HB2 | ALA | 8 | 7.415 | -1.800 | .241   |
| 93  | HB3 | ALA | 8 | 7.675 | -.269  | 1.087  |
| 94  | C   | ALA | 8 | 7.762 | -.755  | -2.355 |
| 95  | O   | ALA | 8 | 7.562 | -.002  | -3.304 |
| 96  | N   | NME | 9 | 7.602 | -2.077 | -2.453 |
| 97  | HN  | NME | 9 | 7.783 | -2.641 | -1.638 |
| 98  | CT  | NME | 9 | 7.166 | -2.736 | -3.673 |
| 99  | HT1 | NME | 9 | 6.431 | -2.126 | -4.201 |
| 100 | HT2 | NME | 9 | 8.026 | -2.904 | -4.322 |
| 101 | HT3 | NME | 9 | 6.712 | -3.695 | -3.424 |

PEPTIDE COMPOSITIONS WITH GROWTH FACTOR-LIKE ACTIVITY

This is a continuation-in-part application of U.S. Ser. No. 08/431,954, filed May 1, 1995 now U.S. Pat. No. 5,661,127, issued Aug. 26, 1997.

FIELD OF THE INVENTION

The invention generally relates to growth factors and neurotrophic factors, and more particularly to small, synthetic peptides having (or mimicking) TGF-β activity, and to matrices and compositions including these small peptide mimics.

BACKGROUND OF THE INVENTION

Growth factors are substances, such as polypeptide hormones, which affect the growth of defined populations of animal cells in vivo or in vitro, but which are not nutrient substances. Proteins involved in the growth and differentiation of tissues may promote or inhibit growth, and promote or inhibit differentiation, and thus the general term "growth factor" includes cytokines and trophic factors.

Growth factors typically are polypeptides ranging in molecular weights from 5000 to 50,000 daltons. Based on structural similarities, growth factors are categorized into families which include: insulin-like growth factors (IGFs), platelet-derived growth factors (PDGFs), fibroblast growth factors (FGFs), epidermal growth factors (EGFs), nerve growth factors (NGFs), and transforming growth factors type-beta (TGF-βs).

Transforming growth factor-βs were originally named for their ability to transform normal fibroblasts to cells capable of anchorage-independent growth. However, despite the name, TGF-βs are multifunctional growth factors that are required for the normal development, growth, and differentiation of various epithelial, endothelial, and mesenchymal cells. As with other cytokines, the specific effect of TGF-βs depend on the particular cell type and its surrounding environment.

The effects of TGF-βs on cells are generally classified as proliferative and non-proliferative. As originally established with the first experiments on fibroblasts, TGF-βs are bona fide growth factors. Two important cell types in which proliferation is enhanced by TGF-β are osteoblasts and Schwann cells of the peripheral nervous system. However, in many cells, TGF-βs are potent inhibitors of cell proliferation. This negative growth control may be the regulatory mechanism that checks regeneration of certain tissues and may play a role in the initiation of carcinogenesis.

The most important non-proliferative function of TGF-βs are in enhancing the formation of extracellular matrices. Although this is achieved primarily through the increased transcription of both collagen and fibronectin, the inhibition of the proteases from degrading the matrix also contributes to its stability. Degradation of the extracellular matrix is inhibited by the decrease in the secretion of the proteases themselves and the simultaneous increase in the levels of protease inhibitors. The marked and generalized effect of TGF-β on extracellular matrices is likely to play a major role in tissue repair processes and the pathogenesis of certain fibrotic diseases.

DNA encoding several different receptors for TGF-β has recently been described by Lin et al., PCT application WO93/09228, published May 13, 1993. The availability of the TGF-β receptors will facilitate further assessments of TGF-β functions.

Many members of the TGF-β super family have been characterized. For example, Basler et al. have graphically represented the sequence relationship between members of the TGF-β superfamily. *Cell*, 73, pp. 687–702 (1993). Massague, *Annu. Rev. Cell Biol.*, 6, pp. 597–641 (1990) also reviews the transforming growth factor-β family, including a discussion of the mechanisms of TGF-β actions. An NMR characterization of the secondary structure of TGF-β1 has been reported, and a refined 3-dimensional crystal structure of TGF-β2 described, by Daopin et al., *Proteins*, 17, pp. 176–192 (1993). The monomer of TGF-β2 adopts a fold that resembles a slightly curled left hand with two anti-parallel β-sheets forming four fingers of the hand. These four finger regions together with conserved disulfides define the fold for the TGF-β superfamily.

Also among TGF-β members are the bone morphogenetic proteins (BMP). The BMPs have been indicated as useful in wound healing, tissue repair, and to induce cartilage and/or bone growth. For example, PCT Application 9309229, inventors Israel and Wolfman, published May 13, 1993, describes uses of proteins with bone stimulating activity such as bone fracture healing and possibly the treatment of periodontal disease and other tooth repair processes. A recent special article by *C&EN*, Hubbell and Langer, pp. 42–54 (Mar. 13, 1995) reports that a BMP has been incorporated into polymer particles so that as the polymer degrades, the protein is slowly released to surrounding tissues, where it stimulates the migration of cells into the porous matrix and, ultimately, the synthesis of new bone. The article also notes that bone has been produced by slowly releasing TGF-β.

Because of the wide applicability of TGF-βs in clinical therapies, they have been the focus of much research. Although much of the research involved in vitro uses, recent in vivo studies have confirmed some of the more promising in vitro effects. As a consequence, some of the possible clinical uses for TGF-βs include the stimulation of angiogenesis, the formation of granulation tissue associated with wound healing, and the formation of bone and cartilage.

Nucleic acid encoding TGF-β and a variety of uses for TGF-β are described in U.S. Pat. No. 5,284,763, issued Feb. 8, 1994, inventors Derynk and Goeddel. U.S. Pat. No. 5,258,029, issued Nov. 2, 1993, inventors Chu et al. describe preparations of stress-bearing prothesis with bony ingrowth occurring after implantation, which prothesis includes TGF-β carried by a collagen composition or a ceramic. U.S. Pat. No. 5,368,858, issued Nov. 29, 1994, inventor Hunziker describes preparations of biodegradable matrices including TGF-βs as proliferation agents, chemotactic agents, and transforming factors.

U.S. Pat. No. 5,055,447, inventors Palladino et al., issued Oct. 8, 1991, describes methods and compositions for the treatment or prophylaxis of septic shock caused by bacteremic infection. Thus, for example, this patent teaches a therapeutic method for a patient suffering from or at risk of septic shock by administering transforming growth factor-β. Recently, the concept of "sepsis" has been viewed more broadly as an inflammatory condition, and a group of researchers have suggested the designation "systemic inflammatory response syndrome" to describe both "sepsis" (infection by the presence of bacteria in the blood stream) as well as other (non-septic) inflammatory conditions. *Chest*, 101, pp. 1644–1655 (1992).

Thus, growth factors are useful in a number of therapeutic, clinical, research, diagnostic, and drug design applications. However, as previously mentioned, growth factors are typically large. The natural members of the transforming growth factor-β family range upwards of 25 KDa molecular weight. Clinical uses of growth factors, including TGF-βs, may be limited because of their size, such as due to causing immune responses. For example, human TGF-β1 is a 25,000 dalton homodimeric protein. In addition to possible adverse immunological responses, large proteins are not often the best candidates for drugs because of the difficulties in administration and delivery.

Consequently, small peptide mimics of natural growth factors which would avoid most of these problems would be desirable for applications including those to which TGF-β has been put or suggested. It would be advantageous to have small peptides mimicking the biological activity of the large, natural members since small peptides on a mole per mole basis would require much smaller net amounts for administration, and topical applications would be more feasible. Also, quite small peptides would tend to have little or no adverse immunological responses, and could be synthesized easily using simple peptide chemistry procedures.

SUMMARY OF THE INVENTION

The present invention describes the characterization, properties, and uses of peptide mimics for TGF-β. Because the critical feature for TGF-β activity is the peptide's ability to maintain a stable β-bend structure under physiologic conditions, the peptides of the present invention are collectively referred to as β-bend peptides.

The β-bend peptides have the following initial amino acid sequence, $AA_i$-$AA_{i+1}$-$AA_{i+2}$ wherein $AA_i$ is alanine, asparagine, or leucine, $AA_{i+1}$ is valine or isoleucine, and $AA_{i+2}$ is alanine. This sequence is either immediately followed by or has proximal thereto an amino acid with a carbonyl containing side-chain. Because the amino acid residue with a carbonyl containing side-chain does not necessarily have to be immediately followed by, that is adjacent to $AA_{i+2}$, it is referred to as $AA_{i+n}$ where n is an integer equal to or greater than three. If n is greater than 3, then n−3 ("n minus 3") amino acid residues would be between $AA_{i+2}$ and $AA_{i+n}$ in the peptide sequence.

For example, the novel β-bend peptide may include the sequence $AA_i$-$AA_{i+1}$-$AA_{i+2}$-$AA_{i+3}$ where $AA_i$ through $AA_{i+2}$ are as before and $AA_{i+3}$ is the amino acid residue with a carbonyl containing side-chain (and is glutamic acid, aspartic acid, glutamine, or asparagine). Another example is the sequence $AA_i$-$AA_{i+1}$-$AA_{i+2}$-$AA_{i+3}$-$AA_{i+4}$ where the residue with the carbonyl containing side-chain is not immediately adjacent, but instead is proximal to, the initial sequence. In this case, $AA_i$ through $AA_{i+2}$ are as before, $AA_{i+3}$ is any suitable amino acid, and $AA_{i+4}$ is glutamic acid, aspartic acid, glutamine, or asparagine. Yet another example is the sequence $AA_i$-$AA_{i+1}$-$AA_{i+2}$-$AA_{i+3}$-$AA_{i+4}$-$AA_{i+5}$. Here, $AA_i$ through $AA_{i+2}$ are as before, $AA_{i+3}$ and $AA_{i+4}$ are suitable amino acids, and $AA_{i+5}$ is glutamic acid, aspartic acid, glutamine, or asparagine.

The original peptide discovered to have TGF-β activity has been named "cytomodulin." An especially preferred embodiment of the present invention, cytomodulin when added to cells in culture in the concentration range $10^{-9}$ to $10^{-6}$M (1.4 pg/mil to 1400 pg/mil), elicits certain highly specific TGF-β effects in several different cell types. For example, among the effects observed is the inhibition of DNA synthesis in Mv-1-Lu mink lung epithelial cells, the growth and colony formation by NRK-49 F fibroblasts in soft agar, and the induction of increased expression of type I collagen in primary cultures of neo-natal human dermal fibroblasts. Moreover, initial results with human osteogenic sarcoma (HOS) cell line indicate that cytomodulin also may be a mimic for other members of the TGF-β superfamily, such as bone morphogenic proteins (BMPS) and osteogenic protein (OPs), as evidenced by its ability to specifically stimulate markers (alkaline phosphatase and osteonectin) characteristic of the osteoblast phenotype.

The novel β-bend peptides are readily synthesized by techniques known to the art. Thus, in one aspect of the present invention, biologically active peptides are provided for eliciting responses characteristic of those elicited by TGF-β.

In another aspect of the present invention, a composition for tissue repair comprises a biocompatible matrix combined with at least one novel β-bend peptide. The biocompatible matrix may be biodegradable or nonbiodegradable. The peptide or peptides are admixed with or carried on the matrix in an amount effective to promote cell growth. Such matrices are useful in constructing templates for repair of soft and hard tissues, for rapid replacement of lost tissue, and for reconstructive and plastic surgery. Such composites provide and sustain cellular regeneration and can be used in combination with other growth factors although surprising, cytomodulin, an especially preferred peptide embodiment of the invention, induces fibroblast colony formation without the presence of additional growth factors such as epidermal growth factor and platelet-derived growth factor.

In yet another aspect of the present invention, a pharmaceutical formulation is provided comprising at least one of the novel β-bend peptide, and a physiologically compatible carrier.

The novel β-bend peptides of the present invention have biological activity that mimic at least one biological activity of TGF-βs, such as inhibiting DNA synthesis in Mv-1-Lu mink lung epithelial cells, promoting growth and colony formation by NRK-49 F fibroblasts, inducing increased expression of type I collagen, and/or inducing TGF-β expression.

BRIEF DESCRIPTION OF THE DRAWINGS

FIG. 5 gives the atomic coordinates for atom numbers 1–101 of the cytomodulin embodiment of the invention;

DESCRIPTION OF THE PREFERRED EMBODIMENTS

Figure 1:
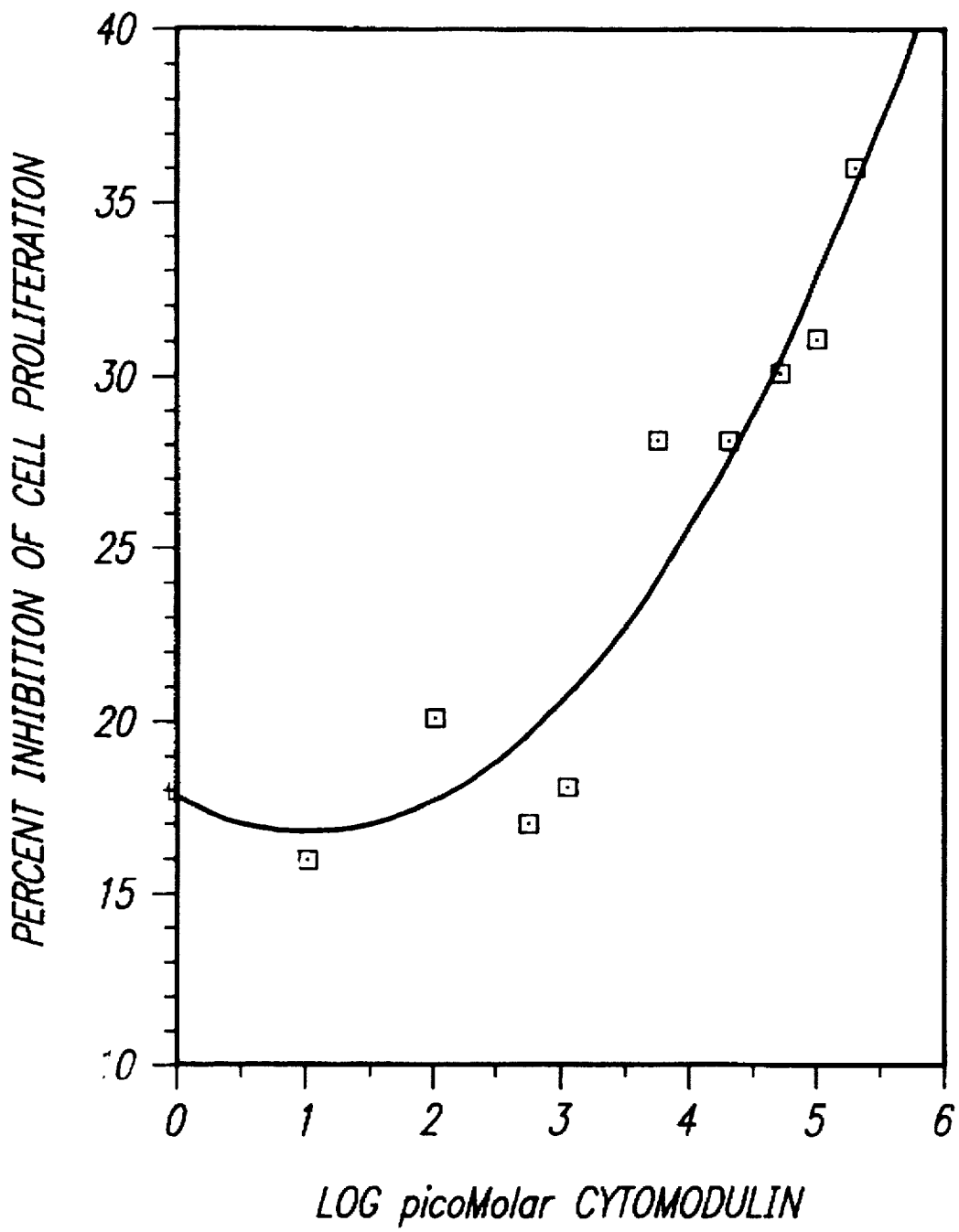
FIG. 1 graphically illustrates the inhibition of DNA synthesis of Mv-1i-Lu mink lung epithelial cells by cytomodulin.

Small peptide mimics of TGF-β have been prepared. Because the critical feature for TGF-β activity is a peptide's ability to maintain a stable β-bend structure under physiologic conditions, the peptides of the present invention are collectively referred to as β-bend peptides.

The inventive peptides have the following initial amino acid sequence, $AA_i$-$AA_{i+1}$-$AA_{i+2}$ wherein $AA_i$ is alanine, asparagine, or leucine, $AA_{i+1}$ is valine or isoleucine, and $AA_{i+2}$ is alanine. This sequence is either immediately followed by or has proximal thereto an amino acid with a carbonyl containing side-chain. Because the amino acid residue with a carbonyl containing side-chain does not necessarily have to be immediately followed by, that is adjacent to $AA_{i+2}$, it is referred to as $AA_{i+n}$ where n is an integer equal to or greater than three. If n is greater than 3, then n–3 ("n minus 3") amino acid residues would be between $AA_{i+2}$ and $AA_{i+n}$ the peptide sequence.

In one embodiment of the invention n equals three and the amino acid residue with the carbonyl containing side-chain is thus $AA_{i+3}$. This results in peptides having the following sequence $AA_i$-$AA_{i+1}$-$AA_{i+2}$-$AA_{i+3}$ wherein $AA_i$, $AA_{i+1}$, and $AA_{i+2}$ are as above and $AA_{i+3}$ is glutamic acid, aspartic acid, glutamine, or asparagine. The original peptide with TGF-β activity and an especially preferred embodiment of the present invention, cytomodulin, Ala-Asn-Val-Ala-Glu-Asn-Ala (SEQ ID. NO:1) is of this class. Here, $AA_i$-$AA_{i+1}$-$AA_{i+2}$-$AA_{i+3}$ corresponds to the second through fifth residues from the N-terminus of cytomodulin, -Asn-Val-Ala-Glu-. Other preferred embodiment are the peptides, Leu-Ile-Ala-Glu-Ala-Lys (SEQ ID. NO:2) and Leu-Ile-Ala-Glu-Ala-Ala (SEQ ID. NO:11). In these examples, $AA_i$-$AA_{i+1}$-$AA_{i+2}$-$AA_{i+3}$ corresponds to the first four residues of the peptide, Leu-Ile-Ala-Glu-.

In another embodiment, n equals four and the amino acid residue with the carbonyl containing side-chain is thus $AA_{i+4}$. The sequence of the peptides of this class is $AA_i$-$AA_{i+1}$-$AA_{i+2}$-$AA_{i+3}$-$AA_{i+4}$. In this series, $AA_i$, $AA_{i+1}$, $AA_{i+2}$ are as above, $AA_{i+3}$ is either proline or glycine, and $AA_{i+4}$ is glutamic acid, aspartic acid, glutamine, or asparagine. A preferred embodiment of this class is Leu-Ile-Ala-Gly-Glu-Gly (SEQ ID. NO:14). An especially preferred embodiment is the peptide, Leu-Ile-Ala-Pro-Glu-Ala (SEQ ID. NO:3). In both examples, the first five N-terminal amino acids correspond to $AA_{i+1}$-$AA_{i+2}$-$AA_{i+3}$-$AA_{i+4}$.

In yet another embodiment of the present invention, n equals five and the amino acid residue with the carbonyl containing side-chain is thus $AA_{i+5}$. The sequence of the peptides of this class is $AA_i$-$AA_{i+1}$-$AA_{i+2}$-$AA_{i+3}$-$AA_{i+4}$-$AA_{i+5}$. In this series, $AA_i$, $AA_{i+1}$, and $AA_{i+2}$ are as above, $AA_{i+3}$ and $AA_{i+4}$ are glycine, and $AA_{i+5}$ is glutamic acid, aspartic acid, glutamine, or asparagine.

An especially preferred member of this series is the peptide, Leu-Ile-Ala-Gly-Gly-Glu (SEQ ID. NO:13). In this particular example there is a one to one correspondence between SEQ ID. NO:3 and the sequence $AA_i$-$AA_{i+1}$-$AA_{i+2}$-$AA_{i+3}$-$AA_{i+4}$-$AA_{i+5}$.

peptides of the present invention can be synthesized by various suitable methods that are well known in the art, preferably by solid phase synthesis, manual or automated, as first developed by Merrifield and described by Stewart et al. in *Solid Phase Peptide Synthesis* (1984). Chemical synthesis joins the amino acids in the predetermined sequence starting at the C-terminus. Basic solid phase methods require coupling the C-terminal protected α-amino acid to a suitable insoluble resin support. Amino acids for synthesis require protection on the α-amino group to ensure proper peptide bond formation with the preceding residue (or resin support). Following completion of the condensation reaction at the carboxyl end, the α-amino protecting group is removed to allow the addition of the next residue. Several classes of α-protecting groups have been described, see Stewart et al. in *Solid Phase Peptide Synthesis* (1984), with the acid labile, urethan-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid sidechain functional groups require blocking until the synthesis is completed. The complex array of functional blocking groups, along with strategies and limitations to their use, have been reviewed by Bodansky in *Peptide Synthesis* (1976) and, Stewart et al. in *Solid Phase Peptide Synthesis* (1984).

Solid phase synthesis is initiated by the coupling of the described C-terminal α-protected amino acid residue. Coupling requires activating agents, such as dicyclohexycarbodiimide (DCC) with or without 1-hydroxybenzo-triazole (HOBT), diisopropylcarbodiimide (DIIPC), or ethyldimethylaminopropylcarbodiimide (EDC). After coupling the C-terminal residue, the α-amino protected group is removed by trifluoroacetic acid (25% or greater) in dichloromethane in the case of acid labile tertiary-butyloxycarbonyl (Boc) groups. A neutralizing step with triethylamine (10%) in dichloro-methane recovers the free amine (versus the salt). After the C-terminal residue is added to the resin, the cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide form the resin and to remove the side chain blocking groups. Anhydrous hydrogen fluoride (HF) cleaves the acid labile tertiary-butyloxycarbonyl (Boc) chemistry groups. Several nucleophilic scavengers, such as dimethylsulfide and anisole, are included to avoid side reactions especially on side chain functional groups.

It is believed that slight amino acid modifications to the β-bend peptide sequences will not affect the peptides' ability to form stable β-bend structures. These modifications include techniques to confer resistance to enzymatic degradation such as adding blocking groups to both the N- and C-terminal residues. Another method for preventing degradation and premature clearance by the renal system is the use of unnatural amino acid substitutes in the peptide sequence. For example, N-methyl-alanine is often substituted for alanine and α-amino isobutryic acid and α-amino butric acid are substitutes for bulky hydrophobic amino acids. Yet another technique is replacing the L-amino acid residue in the peptide sequence with a D-amino acid counterpart. For example, an alanine may be replaced with D-alanine.

The novel β-bend peptides are believed to find uses as agents for enhancing the survival or inducing the growth of nerve and muscle cells. A β-bend peptide is, of course, useful as a new component of culture media for use in culturing nerve cells in vitro. The inventive peptides also have utility as a substitute for the natural cytokines in many fields including: in surgery as agents which promote wound healing and regeneration; in orthopedics in promoting bone repair and implant integration; in dentistry in the repair of bony defects and in implant integration; in cancer chemotherapy and in radiation treatment as cytostatic agents for protection of normal stem cells against cell cycle specific procedures; in treatment of rheumatoid arthritis; in ophthalmology for the repair of macular injury; in ophthalmology for the treatment of uveitis; as a protective agent for splanchnic artery occlusion reperfusion injury; and, as reagents for research in the biology of growth factors.

Therapeutic compositions of this invention will include novel β-bend peptides in concentrations that depend upon the effective doses required and the modes of administration used. Various therapeutic indications for compositions containing at least one β-bend peptide will readily come to mind. One indication is topical application to incisions or exposed tissue for the promotion of wound healing. The types of wound or other traumata that can be treated include (but are not limited to): first, second, and third degree burns (especially second and third degree); epidermal and internal surgical incisions, including those of cosmetic surgery; wounds, including lacerations, incision, and penetrations; and epidermal ulcers including decubital (bed-sores), diabetic, dental, hemophiliac, and varicose.

Uses may be by a variety of methods, such as systemic administration, topical application, intravenous administration, subcutaneous administration, intraperitoneal injection, sub-periosteal injection, intra-tracheal administration, release from polymers or pumps, implants, or release from liposomes. Suitable implants (if using an implanted device) include, for example, gel foam, wax, or microparticle-based implants. Doses used should be sufficient to achieve circulating plasma concentrations of active ingredient that are efficacious. Effective doses may be extrapolated from dose-response curves derived from in vitro or animal model test systems.

The inventive peptides also are useful for inducing growth of bone. Thus, osteogenically effective amounts of at least one β-bend peptide in a pharmaceutically acceptable carrier or excipient can be administered for inducing deposition and maturation of bone at the site. In addition, the peptide or peptides can be admixed with or carried by biomaterials, such as hydroxyapatite for bone generation or repair applications in a method such as is described by U.S. Pat. No. 5,158,934, issued Oct. 27, 1992, U.S. Pat. No. 5,208,219, issued May 4, 1993, by compositions such as described in U.S. Pat. No. 5,178,845, issued Jan. 12, 1993, all incorporated herein by reference.

Such bone repair compositions typically include various calcium phosphate mineral component materials such as, for example, hydroxyapatites commercially available under the designations Synthograft, Tricalcium Phosphate, or Periogras. The hydroxyapatite (or tricalcium phosphate) may be prepared by known methods rather than commercially purchased, such as those disclosed by Termine et al., Arch. Biochem. Biophys., 140, TP307-325 (1970). Such a material can be supplied as a powder with preferred particle sizes typically in the range of about 100-2000μ.

Another therapeutic indication for compositions containing at least one β-bend peptide is in conjunction with matrix forming materials. Preferably, the formulations include a matrix that is capable of providing a structure for developing bone and cartilage. Potential matrices may be biodegradable or nonbiodegradable, and may be chemically or biologically defined.

For one example, the matrix can be inert, solid and non-porous, such as known and presently used as vessels for cell culture. Another form that may be taken by matrices of this invention is that of soluble polymers. Other suitable matrices for practice of this invention include various polymers and hydrogels. Such composites are useful in constructing templates for repair of soft tissue, for rapid replacement of lost tissue, and for reconstructive and plastic surgery.

Composites of the invention can thus be made with resorbable polymers of various kinds, having peptide carried by or grafted onto the lattice of the polymeric material. Of course, polymeric supports that are limited in resorbable properties such as hydroxyethyl methacrylate, polymethylmethacrylate, and N-vinylpyrrolidone methylmethacrylate, as a few examples, are also feasible. The composites can then be implanted in the tissue defect.

Among the known and suitable resorbable hydrogels are combinations of polylactacte and polyglycollate. Compounds of the invention can be covalently bound to such materials during synthesis of the polymers themselves or the polymers can be hydrolyzed such that attachment sites are available by irradiating the polymer or by chemically activating the polymer to generate free radicals. Then conventional techniques for grafting, or immobilizing, peptides onto polymer supports can be utilized to prepare inventive composites. Resorbable hydrogels or polymers so prepared are particularly useful for soft tissue reconstructions. For hard tissue reconstructions or repair (e.g., bone repair) it is desirable to combine such water soluble, or resorbable, polymer species with a bioceramic, such as for example bioglass, aluminum oxide, calcium aluminate, tricalcium phosphate, and hydroxyapatite.

When a β-bend peptide is prepared for administration by mixing with physiologically acceptable carriers, i.e., carriers which are non-toxin to recipients at the dosages and concentrations employed, this will normally entail combining the inventive peptide(s) with buffers, antioxidants such as ascorbic acid, low molecular weight (less than about 10 residues) polypeptides, proteins, amino acids, carbohydrates including glucose or dextrins, chelating agents such as EDTA, and other excipients. The inventive peptide for use in therapeutic administrations must be sterile. This is readily accomplished by filtration through sterile filtration (0.22 micron) membranes.

The novel β-bend peptides may be administered in any pharmacologically acceptable carrier, and depending upon the desired mode of administration, may be formulated along with liquid carrier into liposomes, microcapsules, polymers or wax-based and controlled release preparations, or be formulated into tablet, pill, or capsule forms.

The peptides form pharmaceutically acceptable salts with organic and inorganic acids and can be administered in salt form or the novel β-bend peptide can be amidated. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, benzene-sulfonic, methane- and ethanesulfonic, hydroxymethane- and hydroxyethane-sulfonic.

Salts may also be formed with suitable organic pharmaceutically acceptable base addition salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methyl-glucosamine; N-methyl-glucamine; L-glutamine; N-methylpiperazine;

morpholine; ethylenediamine; N-benzylphenethylamine; tris(hydroxymethyl)aminomethane; and the like. (See, for example, "Pharmaceutical Salts," *J. Pharm. Sci.*, 66(1), 1-19 (1977).)

Therapeutic formulations containing at least one β-bend peptide, such as for promoting bone cell growth, may be prepared for storage by mixing at least one of the novel peptides having the desired degree of purity with optional physiologically acceptable carriers, excipients or stabilizers, in the form of lyophilized cake or aqueous solutions. Acceptable carriers, excipients or stabilizers are nontoxic to recipients at the dosages and concentrations employed when administered, and include buffers such as phosphate, citrate, and other organic acids; anti-oxidants including ascorbic acid; low molecular weight (less than about 10 residues) polypeptides; proteins, such as serum albumin, gelatin or immunoglobulins.

Other components can include glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, PLURONICS or PEG. Yet additional useful components desirably included in therapeutic formulations of cytomodulin are one or more other growth factors, such as, for example, epidermal growth factor (EGF) and platelet-derived growth factor (PDGF).

Initial dosing of the novel β-bend peptides for topical applications such as wound healing should be delivered to the therapeutic site in a concentration of about from 50 to 500 ng/ml and thereafter adjusted in line with clinical experience. Since the inventive compositions both provide and sustain cellular regeneration, a continual application or periodic reapplication of the compositions is indicated. The clinician will be expected to modify the dosage in accordance with clinical experience.

Compositions may be used in the form of a sterile irrigant, preferably in combination with a physiological saline solution, or in the form of ointments or suspensions, preferably in combination with other growth factors as earlier noted, and yet further with collagen, a collagen analogue, or a collagen mimic, such as is described, for example, U.S. Pat. No. 5,354,736, issued Oct. 11, 1994, inventor Bhatnagar, incorporated herein by reference. The compositions also may be impregnated into transdermal patches, plasters, and bandages, preferably in a liquid or semi-liquid form. Automicrobial agents such as silver sulfadiazine should be included in such articles or compositions.

The β-bend peptides also may be administered systemically for the treatment of wounds and similar traumata. Systemic administration is useful provided that there are no, or limited, undesirable side-effects, such as the stimulation of neoplastic cellular growth in patients with cancer. Compositions for systemic administration preferably are formulated as sterile, isotonic parenteral injections or infusions.

The inventive compositions, as earlier described, either with a β-bend peptide alone or in combination with other growth factors, collagen, physiologically acceptable carriers, excipients, or stabilizers as described, may be carried by (or admixed with) a biologically compatible matrix. Matrices of the invention can be porous, and in bead, particulate, or fibrous forms. For example, calcium phosphate materials, such as apatite-based ceramics, have been suggested for producing porous tissue implants or prosthesis materials with micropores sufficient to permit tissue attachment. Thus, a therapeutic application for the compositions of the invention is where the matrix forming material is biodegradable and can be used, for example, in cartilage repair.

Matrix materials useful for filing or otherwise dressing a defect in the cartilage include, for example, fibrinogen (activated with thrombin to form fibrin in the defect or lesion), collagen, gelatin or any other biodegradable material which forms a matrix with pores sufficiently large to allow repair cells to populate and proliferate within the matrix and which can be degraded and replaced with cartilage during the repair process.

The matrices useful in the compositions and methods of this invention may be preformed or may be formed in situ, for example, by polymerizing compounds and compositions such as fibrinogen to form a fibrin matrix. Matrices that may be preformed can include collagen, collagen analogues or collagen mimics (e.g., collagen sponges and collagen fleece), chemically modified collagen, gelatin beads or sponges, gel-forming substances, any other gel forming or composite substance that is composed of a biodegradable matrix material that will fill the tissue or bone defect and allow repair cells to populate the matrix, or mixtures of the above.

Biological activities of the inventive peptides will now be further illustrated by the following examples, which are intended to be illustrative and not limiting.

EXAMPLE 1

Inhibition of DNA Synthesis of Mv-1-Lu Mink Lung Epithelial Cells

The effect of TGF-β and cytomodulin were evaluated by determining the rate of [$^1$]thyidine incorporation into total acid-insoluble DNA and cell number. See generally, Sampath et al., *Journal of Biological Chemistry*, 267, pp. 20352–20362 (1992). DNA synthesis rates were determined in triplicate cultures after 24 hour treatment with various concentrations ($10^{-9}$M to $10^{-6}$M) of either TGF-β or cytomodulin (which was synthesized by the Merrifield method) by adding

[methyl-$^3$H]thymidine (2 μCi/ml, 80 Ci/mmol) for 6 hours before the termination of the culture. Incorporation was terminated by aspiration of the medium, and after washing three times with phosphate-buffered saline, the trichloroacetic acid (10%)-precipitated radioactive DNA was extracted with 1.0% (w/v) sodium dodecyl sulfate, 0.1M NaOH and quantitated by liquid scintillation counting. For cell number determination, $1 \times 10^5$ cells were plated in flasks in MEM containing 10% FBS, and after 24 hours, the growth medium was replaced with serum-free medium containing various conceptions of TGF-β and cytomodulin. Triplicate cultures were harvested every 24 hours for the duration of 7 days, and the cell number was determined by counting cells released by trypsin digestion in a fixed volume hemacytometer.

The growth inhibition curve for cytomodulin were similar to that observed for TGF-β at the same concentration range.

EXAMPLE 2

Growth and Colony Formation by NRK-49 F Fibroblasts in Soft Agar

The original assay for TGF-β, the ability to promote anchorage independent growth of normal fibroblasts is still one of the hallmarks of TGF-β activity. NRK-49 F fibroblasts were grown at 37° C. in DEM supplemented with 10% fetal calf serum. The experiments were performed with culture medium, 10 ng/mg epidermal growth factor (EGF), and 10 ng/ml platelet-derived growth factor (PDGF); however, unlike TGF-β, which does not induce colony formation in the absence of these factors (see, for example, Massagu, *J. Biol. Chem.*, 259, pp. 9756–9761 (1984)), cytomodulin did induce colony formation without these two growth factors. To this, either 100 nM TGF-β (positive control) or 100 nM cytomodulin was added. NRK-49 F fibroblasts ($5 \times 10^4$ cells/ml) were mixed with 0.3% agar were plated on the bottom of 35 mm culture dishes. Colony formation was observed starting on day 3 of culture.

As expected no colonies were formed in those cultures containing only the basic medium. Also, as expected, colonies with TGF-β grew colonies. Surprisingly, the cytomodulin cultures also formed colonies to approximately the same extent as the TGF-β cultures. The growth characteristics of the colonies over time were similar between TGF-β and cytomodulin cultures.

Figure 2A:
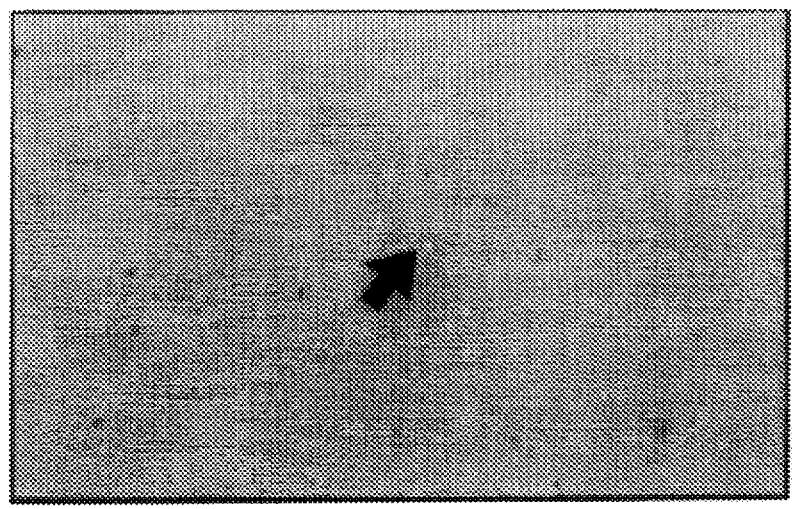
FIG. 2 are photomicrographs (magnification 500 times) wherein Panel (A) is a control, Panel (B) is with 100 nM cytomodulin, and Panel (C) is 100 nM cytomodulin plus EGF and PDGF, all five days in soft agar with NRK-49 F normal rat kidney fibroblasts.
Figure 2B:
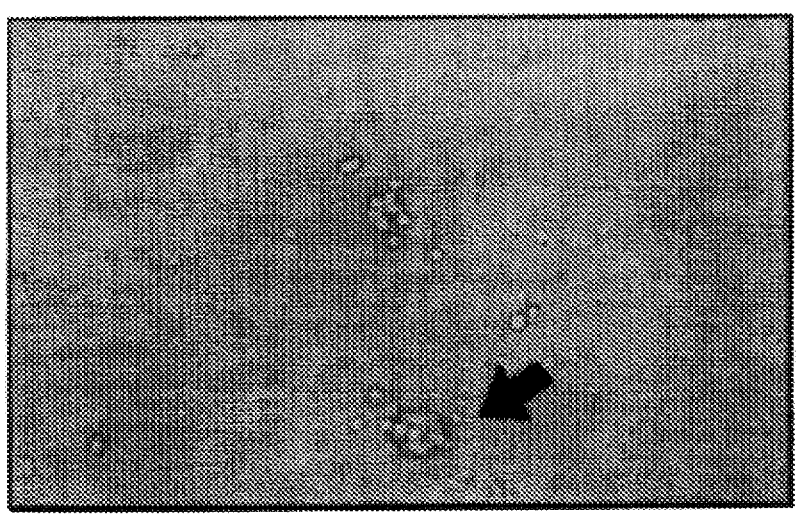
Figure 2C:
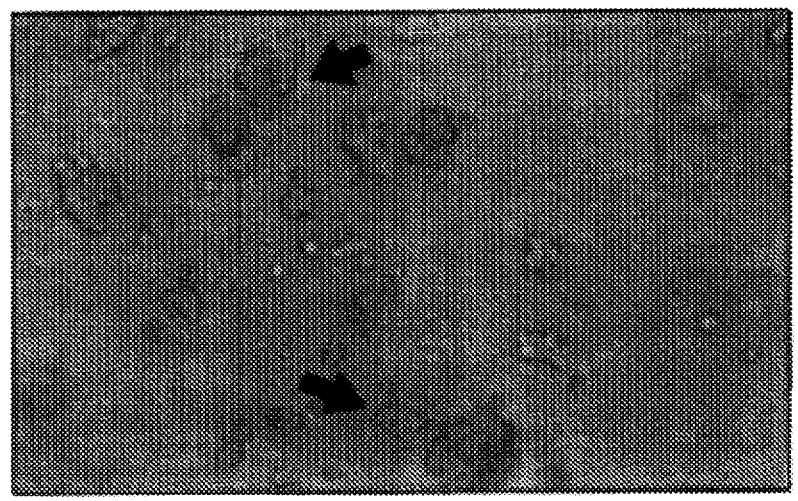
Figure 3B:
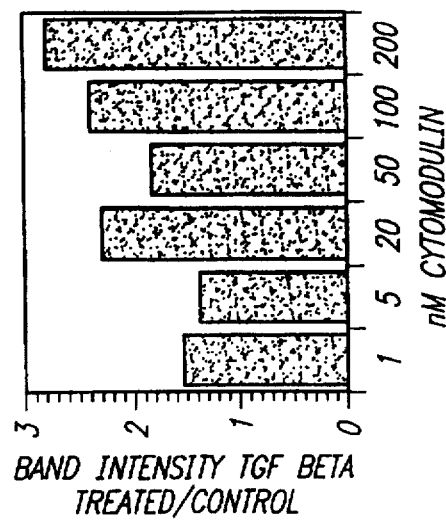
FIG. 3 graphically illustrates the modulation of gene expression in HOS cells by cytomodulin, where Panels (A), (B), and (D) show increased expression while Panel (C) modulated activity depending on concentration, which is however quite characteristic of TGF-β in cells.
Figure 3D:
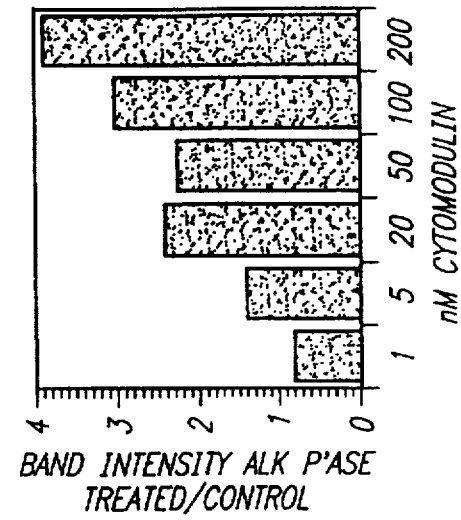
Figure 3A:
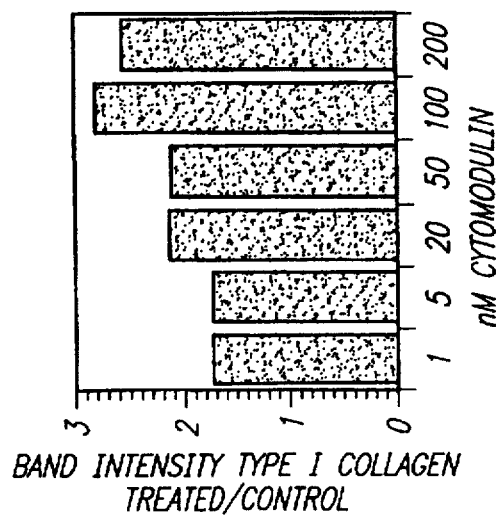
Figure 3C:
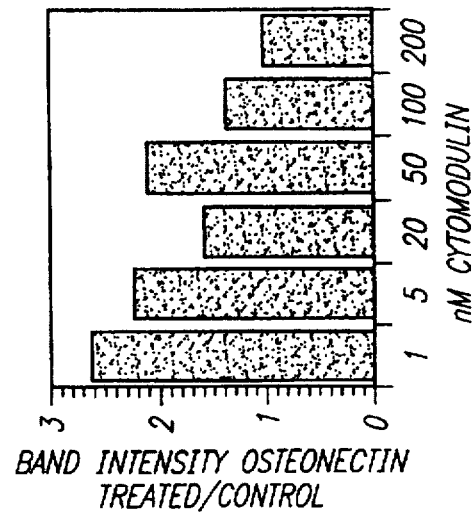
Figure 4A:
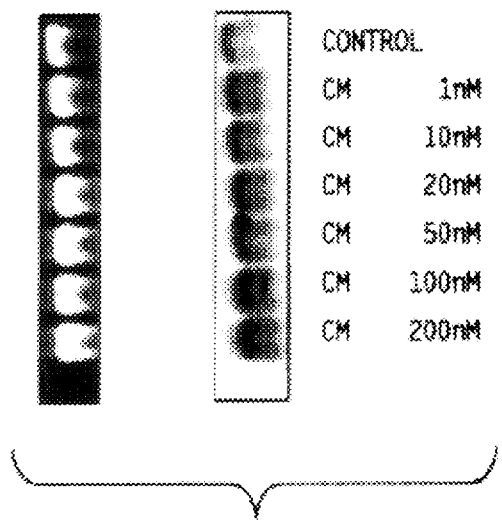
FIG. 4 having panels (A) through (D) are Northern Blots corresponding to the data graphically illustrated by FIG. 3 and its respective panels, (A)–(D)
Figure 4B:
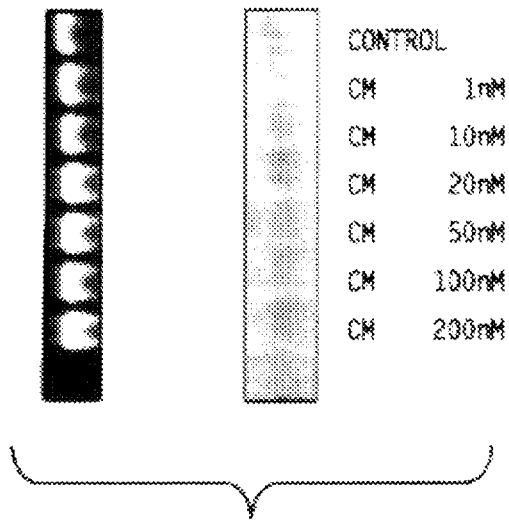
Figure 4C:
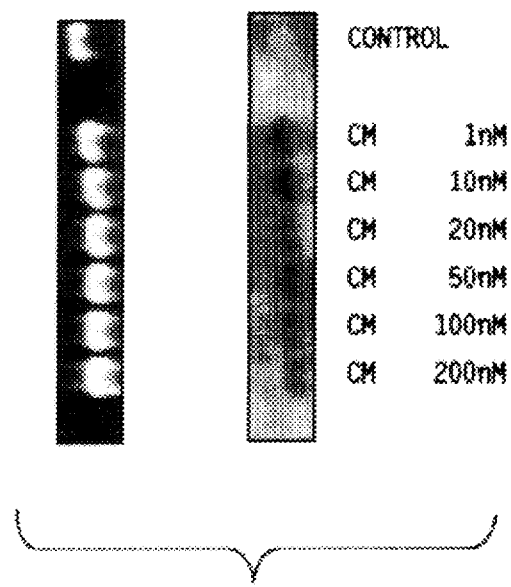
Figure 4D:
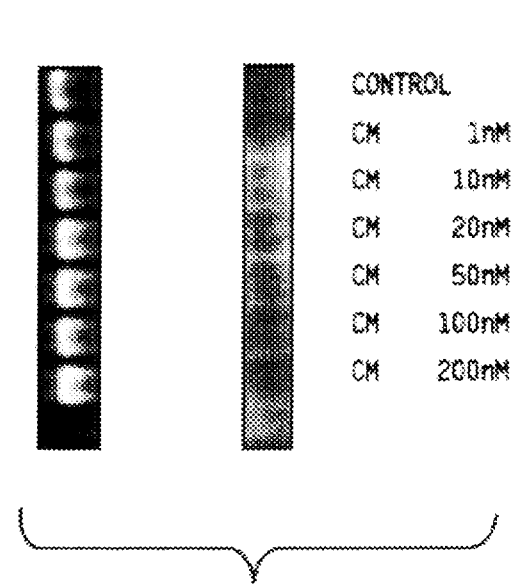

With reference to FIG. 2, photomicrographs are illustrated that were taken on day 5 of the fibroblast culturing. Colony formation was actually observed starting on day 3 of culture. As seen in FIG. 2(A), few cells survived culture in the absence of any growth factors. FIG. 2, Panel (B) and Panel (C) show the formation of small colonies (arrows) in the presence of cytomodulin, with Panel (C) also including EGF and PDGF, which induced much larger colonies (arrows). This is analogous to the induction of colony formation by TGF-β, except that TGF-β requires the concomitant presence of epidermal growth factor (EGF) and platelet derived growth factor (PDGF); however, as seen by Panel (B), cytomodulin did induce colony formation by itself.

EXAMPLE 3

RNA Isolation and Northern Analysis

Total cellular RNA was isolated using essentially the method described by Maniatis, Sambrook et al., *Molecular Cloning: A Laboratory Manual*, Cold Spring Harbor Laboratory Press, Second Edition (1989). Cells were lysed with 0.5% SDS and 0.1 potassium acetate. The lysate was extracted with phenol and centrifuged at 5000 rpm for 15 minutes. The aqueous phase was precipitated with 2 volumes ethanol in 0.1M Tris, pH 8.0 and 0.2M NaCl. The pellet was resuspended and quantitated by measuring the ultraviolet absorbance at 260 nm. RNA purity was assessed by comparing the ultraviolet absorbance at 260 nm with that at 280 nm.

RNA (10 µg/lane) was electrophoresed at 3 to 4 v/cm through a 0.7% agarose, 2.2M formaldehyde denaturing gel. RNA was transferred by capillary transfer to nylon membranes. RNA integrity, gel loading, and transfer efficiency were assessed by methylene blue stained 28S and 18 S bands. The filters were baked at 80° C. for 2 hours to immobilize the RNA. After baking, the filters were hybridized at 65° C. in 0.5M NaPO$_4$ buffer, pH 7.0, containing 1 mM EDTA, 7% sodium dodecyl sulfate, and 1% bovine serum albumin. cDNA probes were labeled with dDIG (fluorescent probe) by the random primer method, using Klenow enzyme. Hybridization for 18 hours at 65° C. followed by washing, was performed.

Data were analyzed by scanning digoxigenin-dVTP according to manufacturer's procedure (Boehringer Mannheim Biochemica, DIG DNA labelling kit, Cat. No. 1175033).

EXAMPLE 4

Stable β-bend required for activity

FIG. 5 shows the atomic coordinates of the bioactive structure of cytomodulin (atoms 1–101). Thus, the structure represented by FIG. 5 describes the β-bend that appears to be necessary for TGF-β activity. Without being limited by theory, if the structure-activity model is correct, analogs having substantially the same structure as cytomodulin will also exhibit TGF-β like activity. Similarly, by exploiting allosteric binding mechanisms, compounds may be synthesized with increased or decreased activity with respect to cytomodulin.

EXAMPLE 5

Using the three dimensional structure of cytomodulin (FIG. 5) as a guide, two initial cytomodulin analogs were designed. From studying the structure, the key features appeared to be the -Val-Ala- sequence responsible for the stable β-bend and a negatively charged side-chain shortly thereafter. At this point, the working structure-activity profile was:

(1) a hydrophobic or neutral amino acid at position i;

(2) a branched hydrophobic at position i+1;

(3) a small aliphatic at position i+2, where positions i+1 and i+2 together form the critical β-bend structure; and (4) a negatively charged side-chain shortly thereafter at either i+3 or i+4 if i+3 is a proline.

To test this hypothesis, two cytomodulin analogs, Leu-Ile-Ala-Glu-Ala-Lys (SEQ. ID. NO:2 or L2) and Leu-Ile-Ala-Pro-Glu-Ala (SEQ. ID. NO:3or L1) were synthesized and tested. In both peptides, -Val-Ala- was replaced by -Ile-Ala- and the first two N-terminal amino acid sequence of cytomodulin was replaced with leucine. In SEQ. ID. NO:3, glutamic acid is at position i+3 since it is the first side-chain after the β-bend structure. In SEQ. ID. NO:4, proline is at position i+3. Since proline does not have a "side-chain," the glutamic acid was placed at position i+4.

Figure 6:
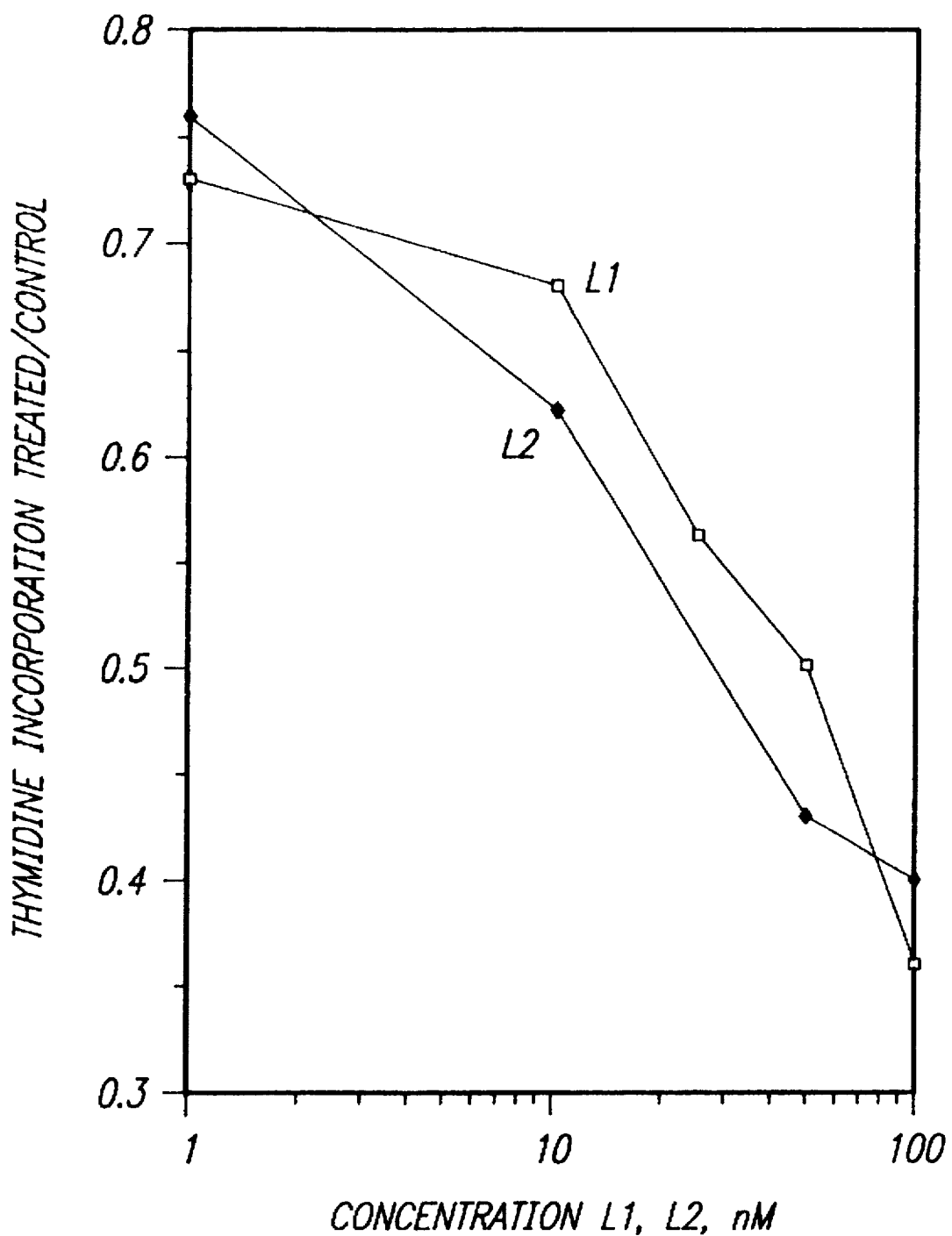
FIG. 6 shows growth inhibition curves of MV-1-Lu cells by cytomodulin analogs, Leu-Ile-Ala-Pro-Glu-Ala (SEQ. ID. NO:3 or "L1") and Leu-Ile-Ala-Glu-Ala-Lys (SEQ. ID. NO:2 or "L2")
Figure 7:
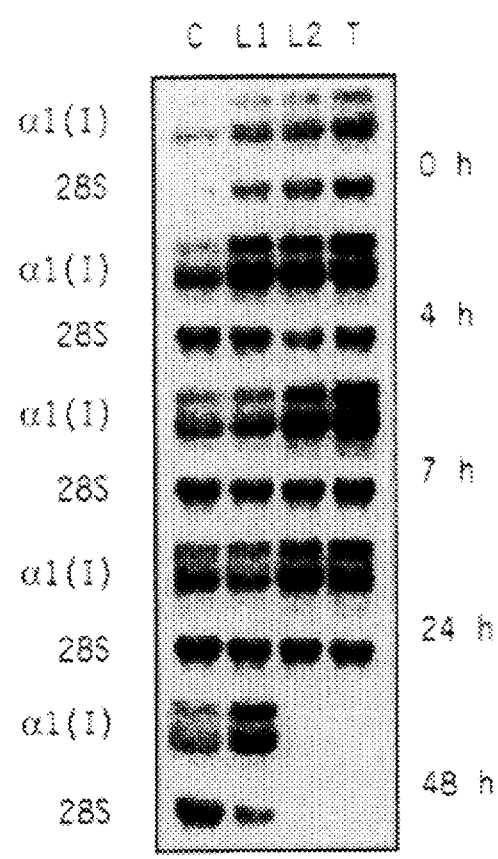
FIG. 7 shows the induction of collagen α1(I) by cytomodulin analogs, L1 and L2, and TGF-β in neonatal human dermal fibroblasts.

Both cytomodulin analogs, L1 and L2, displayed at least as much TGF-β like activity as cytomodulin. They promoted the growth of NRK-49F cells in soft agar and inhibited the proliferation of MV-1-Lu cells (see FIG. 6). They increased the expression of type I collagen and TGF-β (see FIG. 7) and decreased the expression of collagenase in human dermal fibroblasts. Moreover, as with cytomodulin, L1 and L2 also increased the expression of type I collagen, TGF-β and alkaline phosphatase in HOS cells.

EXAMPLE 6

Analogs of SEQ. ID. NO:2 and SEQ. ID. NO:3 were made to further probe the sequence requirements for TGF-β like activity. To that end, the following peptides were made:

Leu-Aib-Ala-Glu-Ala-Lys (SEQ. ID. NO:4)

Leu-Ile-(Nme-Ala)-Glu-Ala-Lys (SEQ. ID. NO:5)

Leu-Abu-Ala-Glu-Ala-Lys (SEQ. ID. NO:6)

Gly-Gly-Gln-Ile-Ala-Asn-Ile (SEQ. ID. NO:7)

Glu-Gly-Ile-Ala-Gly-Lys (SEQ. ID. NO:8)

Leu-Ile-Ala-Asp-Ala-Lys (SEQ. ID. NO:9)

Leu-Ile-Ala-Asn-Ala-Lys (SEQ. ID. NO:10)

Leu-Ile-Ala-Glu-Ala-Ala (SEQ. ID. NO:11)

Leu-Ile-Ala-Gln-Ala-Lys (SEQ. ID. NO:12)

Leu-Ile-Ala-Gly-Gly-Glu (SEQ. ID. NO:13)

Leu-Ile-Ala-Gly-Glu-Gly (SEQ. ID. NO:14)

Ala-Asn-Val-Ala-Glu-Lys (SEQ. ID. NO:15)

Leu-Ile-Ala-Lys-Gly-Lys (SEQ. ID. NO:16)

Of the non-standard amino acids, Aib is α-amino isobutyric acid, Nme-Ala is N-methyl alanine and Abu is α-amino butyric acid.

SEQ. ID. NOs:4–6, which are minor variants of SEQ. ID. NO:2, mimicked the biological activities of TGF-β and cytomodulin as shown by the inhibition of the proliferation of Mv-1-Lu epithelial cells and increased expression of collagen I and TGF-β in HOS cells. Sample thymidine incorporation data for SEQ. ID. NOs:4–6 are shown in Table 1.

TABLE 1

Inhibition of Incorporation of ³H-thymidine in MV-1 Lu cells in the Presence of Test Peptides

| Control (No peptides added) | ³H-Radioactivity, 10³ dpm (% Inhibition) |
|---|---|
|  | 3.57 (-) |
| (IV) LAibAEAK (SEQ. ID. NO: 4) | |
| 1 nM | 2.60 (27%) |
| 5 nM | 2.31 (35%) |
| 50 nM | 1.94 (46%) |
| 100 nM | 1.44 (60%) |
| 500 nM | 1.61 (55%) |
| (V) LINmeAEAK (SEQ. ID. NO: 5) | |
| 1 nM | 1.61 (47%) |
| 5 nM | 1.76 (42%) |
| 50 nM | 1.60 (41%) |
| 100 nM | 1.81 (40%) |
| 500 nM | 1.42 (53%) |
| (VI) LAbuAEAK (SEQ. ID. NO: 6) | |
| 1 nM | 2.02 (33%) |
| 5 nM | 1.97 (35%) |

However, SEQ. ID. NOs:7–8 did not display significant TGF-β activity. This was not unexpected given the working model. An amino acid with a negatively charged side-chain is not present in SEQ. ID. NO:7. Although a glutamic acid is present in SEQ. ID. NO:8, it is on the N-terminal side of the β-bend and not on the C-terminal side as with cytomodulin, L1, and L2.

Inhibition of ³H-thymidine incorporation results for SEQ ID. NOs:9–16 are shown in Table 2. The numbers shown at the various concentration are the ratio of the inhibition rate of the peptide being tested over the inhibition rate of cytomodulin (SEQ. ID. NO:1) at the same concentration. Because cytomodulin inhibits the proliferation of MV-1-Lu cells at least as much as TFG-β, cytomodulin and not TGF-β was used as a control.

TABLE 2

Growth Inhibition Activity of Inventive Peptides

| Peptide Composition | Concentration (nM) | Inhibition in comparison to cytomodulin (Inhib by new peptide/Inhib by cytomodulin) | | | |
|---|---|---|---|---|---|
|  |  | 1 | 10 | 100 | 1000 |
| LIADAK | SEQ. ID. NO: 9 | 0.45 | 0.87 | 1.14 | 1.25 |
| LIANAK | SEQ. ID. NO: 10 | 1.70 | 2.00 | 1.43 | 3.05 |
| LIAEAA | SEQ. ID. NO: 11 | 1.16 | 1.00 | 1.17 | 1.85 |
| LIAQAK | SEQ. ID. NO: 12 | 0.90 | 1.10 | 0.80 | 1.56 |
| LIAGGE | SEQ. ID. NO: 13 | 1.10 | 1.33 | 1.45 | 1.90 |
| LIAGEG | SEQ. ID. NO: 14 | 0.66 | 0.85 | 1.41 | 1.88 |
| ANVAEK | SEQ. ID. NO: 15 | — | 0.80 | 1.00 | — |
| LIAKGK | SEQ. ID. NO: 16 | — | 0.65 | 0.67 | — |

As illustrated by Table 2, all peptides with sequences represented by SEQ. ID. NOs:9–16 inhibited at least some amount of thymidine uptake. From these results, the general model for preparing peptides with TGF-β activity appears to work surprisingly well.

One peptide in particular is especially noteworthy. SEQ. ID. NO:10, Leu-Ile-Ala-Asn-Ala-Lys, inhibited the proliferation of Mv-1-Lu epithelial cells even more than cytomodulin at every concentration tested. Because SEQ. ID. NO:10does not contain a negatively charged side-chain, the working model clearly had to be redefined. Based upon the inhibition activities of both SEQ. ID. NOs:10 and 12 where asparagine and glutamine replaced glutamic acid, the carbonyl group (C=O) appears to be the critical feature and not necessarily the entire carboxylic acid group (COO—).

Another interesting set of peptides is SEQ. ID. NOs:13–14 which explore the positional requirements of the carbonyl group. The activities of these peptides appear to be the result of the unusual flexibility of the glycine backbone. Because glycine's backbone may sample virtually all allowable torsional angles, a carbonyl containing side-chain placed proximal to the β-bend structure could attain its necessary conformation without incurring a significant energy cost. Since SEQ. ID. NO:13would be more flexible than SEQ. ID. NO:14, it is not surprising that SEQ. ID. NO:13inhibits thymidine uptake more than SEQ. ID. NO:14.

Another noteworthy feature includes SEQ. ID. NO:11. Since this peptide displays at least as much activity as cytomodulin, the C-terminal lysine of L1 and L2 are clearly not important. As a result, the structure activity relationship required for TFG-β activity appears to be:

(1) a hydrophobic or neutral amino acid at position i;

(2) a branched hydrophobic at position i+1 (i.e. Val, Ile);

(3) a small aliphatic at position i+2 (i.e. Ala), where positions i+1 and i+2 together form the critical β-bend structure; and (4) a carbonyl containing side-chain shortly thereafter.

It is to be understood that while the invention has been described above in conjunction with preferred specific embodiments, the description and examples are intended to illustrate and not limit the scope of the invention, which is defined by the scope of the appended claims.

It is claimed:

1. A peptide having the sequence $AA_i\text{-}AA_{i+1}\text{-}AA_{i+2}$ or having the sequence $Ala\text{-}AA_i\text{-}AA_{i+1}\text{-}AA_{i+2}$, said peptide further having an $AA_{i+n}$ adjacent or proximal to said sequence in the C-terminus direction, wherein n is 3, 4, or 5 such that said peptide contains n−3 additional amino acid residues in between $AA_{i+2}$ and $AA_{i+n}$ and wherein $AA_i$ is alanine, asparagine, or leucine, $AA_{i+1}$ is valine, isoleucine, α-amino isobutyric acid, or α-amino butyric acid, $AA_{i+2}$ is alanine or N-methyl alanine, and $AA_{i+n}$ is glutamic acid, aspartic acid, glutamine, or asparagine, whereby the peptide forms a stable β-bend structure in physiologic conditions under which TGF-β has a stable β-bend and elicits at least one biological activity of TGF-β.

2. A six or seven amino acid peptide comprising the peptide of claim 1 wherein n is 3 and the peptide sequence further comprises $AA_{i+4}\text{-}AA_{i+5}$ wherein $AA_{i+4}$ and $AA_{i+5}$ are alanine.

3. The peptide as in claim 1 wherein n is 4 and the amino acid residue in between $AA_{i+2}$ and $AA_{i+n}$ is proline or glycine.

4. The peptide as in claim 1 wherein n is 5 and the two amino acid residues in between $AA_{i+2}$ and $AA_{i+n}$ are glycine.

5. A biologically active peptide selected from the group consisting of:

| | |
|---|---|
| Leu—Ile—Ala—Glu—Ala—Lys | (SEQ. ID, NO:2), |
| Leu—Ile—Ala—Pro—Glu—Ala | (SEQ. ID, NO:3), |
| Leu—Aib—Ala—Glu—Ala—Lys | (SEQ. ID, NO:4), |
| Leu—Ile—(N-methyl-Ala)—Glu—Ala—Lys | (SEQ. ID, NO:5), |
| Leu—Abu—Ala—Glu—Ala—Lys | (SEQ. ID, NO:6), |
| Leu—Ile—Ala—Asp—Ala—Lys | (SEQ. ID, NO:9), |
| Leu—Ile—Ala—Asn—Ala—Lys | (SEQ. ID, NO:10), |
| Leu—Ile—Ala—Glu—Ala—Ala | (SEQ. ID, NO:11), |
| Leu—Ile—Ala—Gln—Ala—Lys | (SEQ. ID, NO:12), |
| Leu—Ile—Ala—Gly—Gly—Glu | (SEQ. ID, NO:13), |
| Leu—Ile—Ala—Gly—Glu—Gly | (SEQ. ID, NO:14), |
| and, | |
| Ala—Asn—Val—Ala—Glu—Lys | (SEQ. ID, NO:15). |

6. A composition useful for tissue repair comprising:

a biocompatible matrix; and, a peptide having the sequence $AA_i\text{-}AA_{i+1}\text{-}AA_{i+2}$ or having the sequence $Ala\text{-}AA_i\text{-}AA_{i+1}\text{-}AA_{i+2}$, said peptide further having an $AA_{i+n}$ adjacent or proximal to said sequence in the C-terminus direction, wherein n is 3, 4, or 5 such that said peptide contains n−3 additional amino acid residues in between $AA_{i+2}$ and $AA_{i+n}$ and wherein $AA_i$ is alanine, asparagine, or leucine, $AA_{i+1}$ is valine, isoleucine, α-amino isobutyric acid, or α-amino butyric acid, $AA_{i+2}$ is alanine, and $AA_{i+n}$ is glutamic acid, aspartic acid, glutamine, or asparagine, whereby the peptide forms a stable β-bend structure in physiologic conditions under which TGF-β has a stable β-bend, the peptide admixed with or carried on the matrix and in an amount effective to promote cell growth, the matrix optionally including Ala-Asn-Val-Ala-Glu-Asn-Ala (SEQ ID NO:1).

7. A composition useful for tissue repair comprising:

a biocompatible matrix; and, a six or seven amino acid peptide comprising the peptide as in claim 6 wherein n is 3 and the peptide sequence further comprises $AA_{i+4}\text{-}AA_{i+5}$ wherein $AA_{i+4}$ and $AA_{i+5}$ are alanine.

8. The composition as in claim 6 wherein n is 4 and the amino acid residue in between $AA_{i+2}$ and $AA_{i+n}$ is proline or glycine.

9. The composition as in claim 6 wherein n is 5 and the two amino acid residues in between $AA_{i+2}$ and $AA_{i+n}$ are glycine.

10. The composition as in claim 6 wherein the biocompatible matrix is biodegradable.

11. The composition as in claim 10 wherein the matrix includes a resorbable polymer.

12. The composition as in claim 6 wherein the biocompatible matrix is non-biodegradable.

13. The composition as in claim 12 wherein the matrix is porous.

14. A composition useful for tissue repair, comprising:

a biocompatible matrix; and, a biologically active peptide selected from the group consisting of

| | |
|---|---|
| Leu—Ile—Ala—Glu—Ala—Lys | (SEQ. ID. NO:2), |
| Leu—Ile—Ala—Pro—Glu—Ala | (SEQ. ID. NO:3), |
| Leu—Aib—Ala—Glu—Ala—Lys | (SEQ. ID. NO:4), |
| Leu—Ile—(N-methyl-Ala)—Glu—Ala—Lys | (SEQ. ID. NO:5), |
| Leu—Abu—Ala—Glu—Ala—Lys | (SEQ. ID. NO:6), |
| Leu—Ile—Ala—Asp—Ala—Lys | (SEQ. ID. NO:9), |
| Leu—Ile—Ala—Asn—Ala—Lys | (SEQ. ID. NO:10), |
| Leu—Ile—Ala—Glu—Ala—Ala | (SEQ. ID. NO:11), |
| Leu—Ile—Ala—Gln—Ala—Lys | (SEQ. ID. NO:12), |
| Leu—Ile—Ala—Gly—Gly—Glu | (SEQ. ID. NO:13), |
| Leu—Ile—Ala—Gly—Glu—Gly | (SEQ. ID. NO:14), and, |
| Ala—Asn—Val—Ala—Glu—Lys | (SEQ. ID. NO:15), | the biologically active peptide admixed with or carried on the matrix and in an amount effective to promote cell growth.

15. The composition as in claim 14 wherein the biocompatible matrix is biodegradable.

16. The composition as in claim 15 wherein the matrix includes a resorbable polymer.

17. The composition as in claim 14 wherein the biocompatible matrix is non-biodegradable.

18. The composition as in claim 17 wherein the matrix is porous.

19. A pharmaceutical formulation comprising:

a physiologically acceptable carrier; and, a peptide having the sequence $AA_i$-$AA_{i+1}$-$AA_{i+2}$ or having the sequence Ala-$AA_i$-$AA_{i+1}$-$AA_{i+2}$, said peptide further having an $AA_{i+n}$ adjacent or proximal to said sequence in the C-terminus direction, wherein n is 3, 4, or 5 such that said peptide contains n–3 additional amino acid residues in between $AA_{i+2}$ and $AA_{i+n}$ and wherein $AA_i$ is alanine, asparagine, or leucine, $AA_{i+1}$ is valine, isoleucine, α-amino isobutyric acid, or α-amino butyric acid, $AA_{i+2}$ is alanine or N-methyl alanine, and $AA_{i+n}$ is glutamic acid, aspartic acid, glutamine, or asparagine, whereby the peptide forms a stable β-bend structure in physiologic conditions under which TGF-β has a stable β-bend and elicits at least one biological activity of TGF-β.

20. A pharmaceutical formulation comprising:

a physiologically acceptable carrier; and, a six or seven amino acid peptide comprising the peptide as in claim 19 wherein n is 3 and the peptide sequence further comprises $AA_{i+4}$-$AA_{i+5}$ wherein $AA_{i+4}$ and $AA_{i+5}$ are alanine.

21. The formulation as in claim 19 wherein n is 4 and the amino acid residue in between $AA_{i+2}$ and $AA_{i+n}$ is proline or glycine.

22. The formulation as in claim 19 wherein n is 5 and the two amino acid residues in between $AA_{i+2}$ and $AA_{i+n}$ are glycine.

23. The formulation as in claim 19 wherein the peptide is in the form of a salt.

24. A pharmaceutical formulation, comprising:

a physiologically acceptable carrier; and, a peptide selected from a group consisting of

| | |
|---|---|
| Leu—Ile—Ala—Glu—Ala—Lys | (SEQ. ID, NO:2), |
| Leu—Ile—Ala—Pro—Glu—Ala | (SEQ. ID, NO:3), |
| Leu—Aib—Ala—Glu—Ala—Lys | (SEQ. ID, NO:4), |
| Leu—Ile—(N-methyl-Ala)—Glu—Ala—Lys | (SEQ. ID, NO:5), |
| Leu—Abu—Ala—Glu—Ala—Lys | (SEQ. ID, NO:6), |
| Leu—Ile—Ala—Asp—Ala—Lys | (SEQ. ID, NO:9), |
| Leu—Ile—Ala—Asn—Ala—Lys | (SEQ. ID, NO:10), |
| Leu—Ile—Ala—Glu—Ala—Ala | (SEQ. ID, NO:11), |
| Leu—Ile—Ala—Gln—Ala—Lys | (SEQ. ID, NO:12), |
| Leu—Ile—Ala—Gly—Gly—Glu | (SEQ. ID, NO:13), |
| Leu—Ile—Ala—Gly—Glu—Gly | (SEQ. ID, NO:14), and, |
| Ala—Asn—Val—Ala—Glu—Lys | (SEQ. ID, NO:15). |

25. The formulation as in claim 24 wherein the peptide is in the form of a salt.

* * * * *

UNITED STATES PATENT AND TRADEMARK OFFICE
CERTIFICATE OF CORRECTION

PATENT NO.   : 5,780,436
DATED        : July 14, 1998
INVENTOR(S)  : Bhatnagar, R.S. and Qian, J.J.

Page 1 of 1

It is certified that error appears in the above-identified patent and that said Letters Patent is hereby corrected as shown below:

Column 21,
Line 24, after "$AA_{i+2}$," please insert -- as an initial sequence defining the N-terminus--; and Column 22,
Line 23, after "$AA_{i+2}$," please insert -- as an initial sequence defining the N-terminus--; and Column 23,
Line 29, after "$AA_{i+2}$," please insert -- as an initial sequence defining the N-terminus--.

Signed and Sealed this

Twenty-fourth Day of December, 2002

JAMES E. ROGAN
*Director of the United States Patent and Trademark Office*

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
      ( A ) LENGTH: 7 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:1:

Ala Asn Val Ala Glu Asn Ala
   1               5

( 2 ) INFORMATION FOR SEQ ID NO:2:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:2:

Leu Ile Ala Glu Ala Lys
   1               5

( 2 ) INFORMATION FOR SEQ ID NO:3:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:3:

Leu Ile Ala Pro Glu Ala
   1               5

( 2 ) INFORMATION FOR SEQ ID NO:4:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:4:

Leu Xaa Ala Glu Ala Lys
   1               5

( 2 ) INFORMATION FOR SEQ ID NO:5:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear (ii) MOLECULE TYPE: peptide (xi) SEQUENCE DESCRIPTION: SEQ ID NO:5:

Leu Ile Xaa Glu Ala Lys
1               5

(2) INFORMATION FOR SEQ ID NO:6:

(i) SEQUENCE CHARACTERISTICS:
 (A) LENGTH: 6 amino acids
 (B) TYPE: amino acid
 (C) STRANDEDNESS:
 (D) TOPOLOGY: linear (ii) MOLECULE TYPE: peptide (xi) SEQUENCE DESCRIPTION: SEQ ID NO:6:

Leu Xaa Ala Glu Ala Lys
1               5

(2) INFORMATION FOR SEQ ID NO:7:

(i) SEQUENCE CHARACTERISTICS:
 (A) LENGTH: 7 amino acids
 (B) TYPE: amino acid
 (C) STRANDEDNESS:
 (D) TOPOLOGY: linear (ii) MOLECULE TYPE: peptide (xi) SEQUENCE DESCRIPTION: SEQ ID NO:7:

Gly Gly Gln Ile Ala Asn Ile
1               5

(2) INFORMATION FOR SEQ ID NO:8:

(i) SEQUENCE CHARACTERISTICS:
 (A) LENGTH: 6 amino acids
 (B) TYPE: amino acid
 (C) STRANDEDNESS:
 (D) TOPOLOGY: linear (ii) MOLECULE TYPE: peptide (xi) SEQUENCE DESCRIPTION: SEQ ID NO:8:

Glu Gly Ile Ala Gly Lys
1               5

(2) INFORMATION FOR SEQ ID NO:9:

(i) SEQUENCE CHARACTERISTICS:
 (A) LENGTH: 6 amino acids
 (B) TYPE: amino acid
 (C) STRANDEDNESS:
 (D) TOPOLOGY: linear (ii) MOLECULE TYPE: peptide (xi) SEQUENCE DESCRIPTION: SEQ ID NO:9:

Leu Ile Ala Asp Ala Lys
1               5

(2) INFORMATION FOR SEQ ID NO:10:

(i) SEQUENCE CHARACTERISTICS:
 (A) LENGTH: 6 amino acids
 (B) TYPE: amino acid
 (C) STRANDEDNESS:
 (D) TOPOLOGY: linear ( i i ) MOLECULE TYPE: peptide ( x i ) SEQUENCE DESCRIPTION: SEQ ID NO:10:

Leu Ile Ala Asn Ala Lys
1                   5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:11:

Leu Ile Ala Glu Ala Ala
1                   5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:12:

Leu Ile Ala Gln Ala Lys
1                   5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

Leu Ile Ala Gly Gly Glu
1                   5

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:14:

Leu Ile Ala Gly Glu Gly
1                   5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear

```
( i i ) MOLECULE TYPE: peptide ( x i ) SEQUENCE DESCRIPTION: SEQ ID NO:15:

Ala  Asn  Val  Ala  Glu  Lys
    1                   5

( 2 ) INFORMATION FOR SEQ ID NO:16:

( i ) SEQUENCE CHARACTERISTICS:
          ( A ) LENGTH: 6 amino acids
          ( B ) TYPE: amino acid
          ( C ) STRANDEDNESS:
          ( D ) TOPOLOGY: linear ( i i ) MOLECULE TYPE: peptide ( x i ) SEQUENCE DESCRIPTION: SEQ ID NO:16:

Leu  Ile  Ala  Lys  Gly  Lys
    1                   5
```